United States Patent
Seal et al.

(10) Patent No.: US 7,791,150 B1
(45) Date of Patent: Sep. 7, 2010

(54) ROOM TEMPERATURE HYDROGEN SENSOR

(75) Inventors: Sudipta Seal, Oviedo, FL (US); Satyajit V. Shukla, Orlando, FL (US); Lawrence Ludwig, Merritt Island, FL (US); Hyoung Cho, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 1717 days.

(21) Appl. No.: 10/949,600

(22) Filed: Sep. 25, 2004

(51) Int. Cl.
*H01L 29/06* (2006.01)

(52) U.S. Cl. .................. 257/414; 257/467; 257/619; 257/E21.521

(58) Field of Classification Search ............... 438/14, 438/15, 17, 48, 49; 257/E21.521, 414, 619, 257/467
See application file for complete search history.

(56) References Cited

U.S. PATENT DOCUMENTS

| | | | | |
|---|---|---|---|---|
| 4,397,888 A * | 8/1983 | Yannopoulos et al. | ......... | 438/49 |
| 5,367,283 A * | 11/1994 | Lauf et al. | ..................... | 338/34 |
| 5,385,709 A | 1/1995 | Wise et al. | ..................... | 422/98 |
| 6,006,582 A | 12/1999 | Bhandari et al. | ............. | 73/23.2 |
| 6,036,876 A | 3/2000 | Chen et al. | ..................... | 216/67 |
| 6,041,643 A | 3/2000 | Stokes et al. | ............... | 73/31.06 |
| 6,161,421 A | 12/2000 | Fang et al. | ................. | 73/31.05 |
| 6,265,222 B1 * | 7/2001 | DiMeo et al. | ............... | 436/144 |
| 6,293,137 B1 | 9/2001 | Liu et al. | .................... | 73/31.06 |
| 6,344,417 B1 | 2/2002 | Usenko | ...................... | 438/733 |
| 6,484,563 B1 | 11/2002 | Enquist et al. | ............... | 73/1.02 |
| 6,539,774 B1 | 4/2003 | Zinck et al. | .................. | 73/23.2 |
| 6,548,382 B1 | 4/2003 | Henley et al. | ............... | 438/526 |
| 6,596,236 B2 | 7/2003 | DiMeo, Jr. et al. | ............ | 422/88 |
| 6,597,109 B1 * | 7/2003 | Arai et al. | .................... | 313/506 |
| 6,634,213 B1 | 10/2003 | O'Connor et al. | .......... | 73/31.06 |
| 6,746,886 B2 | 6/2004 | Duncan et al. | ................ | 438/27 |
| 7,009,376 B2 * | 3/2006 | Chou et al. | ................ | 324/71.1 |
| 2002/0142478 A1 * | 10/2002 | Wado et al. | ................ | 436/151 |
| 2003/0153088 A1 | 8/2003 | DiMeo, Jr. et al. | .......... | 436/113 |
| 2004/0074285 A1 | 4/2004 | DiMeo, Jr. et al. | ......... | 73/31.05 |
| 2005/0247961 A1 * | 11/2005 | Zhou | .......................... | 257/213 |

* cited by examiner

*Primary Examiner*—Michael Trinh
(74) *Attorney, Agent, or Firm*—Brian S. Steinberger; Law Offices of Brian S. Steinberger, P.A.

(57) ABSTRACT

A sensor for selectively determining the presence and measuring the amount of hydrogen in the vicinity of the sensor. The sensor comprises a MEMS device coated with a nanostructured thin film of indium oxide doped tin oxide with an over layer of nanostructured barium cerate with platinum catalyst nanoparticles. Initial exposure to a UV light source, at room temperature, causes burning of organic residues present on the sensor surface and provides a clean surface for sensing hydrogen at room temperature. A giant room temperature hydrogen sensitivity is observed after making the UV source off. The hydrogen sensor of the invention can be usefully employed for the detection of hydrogen in an environment susceptible to the incursion or generation of hydrogen and may be conveniently used at room temperature.

18 Claims, 5 Drawing Sheets

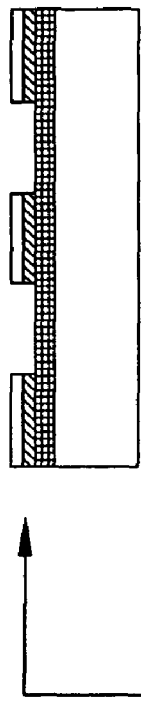
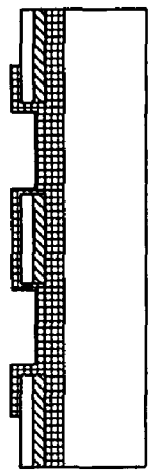
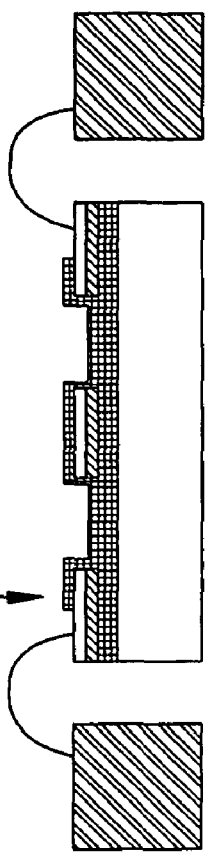
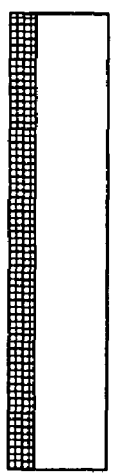
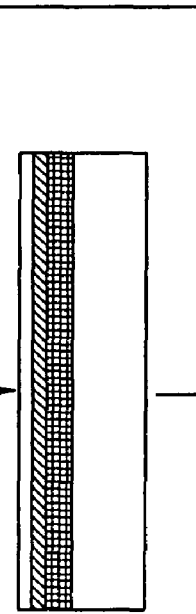

ROOM TEMPERATURE HYDROGEN SENSOR

This invention relates to a room temperature hydrogen sensor, and more specifically to a room temperature hydrogen sensor, which uses micro electro-mechanical systems (MEMS) device, an ultraviolet (UV) radiation, and the nanocstructured indium oxide ($In_2O_3$) doped tin-oxide ($SnO_2$) thin film as a hydrogen sensor with the nanostrucured inorganic thin film H and metal catalyst as hydrogen separation membrane overlayers to selectively detect hydrogen gas in the environment at room temperature.

BACKGROUND AND PRIOR ART

Hydrogen is a flammable and explosive gas with a wide variety of industrial and scientific uses. It is axiomatic that handling hydrogen requires utilization of robust safety devices since hydrogen is a highly flammable gas at concentrations in air as low as 4% by volume. Well-known industrial uses of hydrogen include the production of basic staple products of the chemical industry such as ammonia and fertilizers derived there from. Other uses include basic alcohols, hydrogen chloride, reduction of ores for the manufacturing of metals, refinery of oil for the manufacturing of petroleum, and the hydrogenation of vegetable oils for margarine and related industries.

Hydrogen is also widely used for space flight applications, for example, hydrogen is used as a component of hydrogen-oxygen blends used in vehicular propulsion systems. Hydrogen gas is also used in the processing of rocket fuel in the aerospace industry. The combustible nature of hydrogen however, makes its detection vitally important.

Hydrogen is also utilized in a variety of metal forming and microelectronic processing steps which are often of extreme importance in device fabrication and metal interconnect processing of multi-level microelectronic devices.

The increase in oil prices also increased the emphasis on the use of fuel cells, which require hydrogen as a fuel in various stationary and mobile applications, for instance, in fuel cells of automobiles.

In these and other applications, hydrogen sensors are employed to monitor the environment around which hydrogen is utilized, to ensure the efficiency, safety and operational integrity of process systems. For such purposes, a number of hydrogen sensors and complex detection methods have been developed and are in common use. About one-half of all the sensors used to measure hazardous gases measure hydrogen. The bulk of these systems utilize as the detector element a Group VIIIB metal element, for example, Ni, Pd, or Pt, heated to catalytically oxidize the hydrogen, with the resulting change in heat load being the measured parameter for determination of the presence of hydrogen.

A variety of these commercially available hydrogen sensors are based on measuring an electrical characteristic across a sensor element and at least four major categories of sensors and associated methods have been identified.

One type of hydrogen sensor is the "catalytic combustible" or "hot wire" sensor (CC sensor) mentioned in the U.S. Pat. No. 6,006,582 to Bhandari, et. al. The CC sensor comprises two specially arranged beads of a catalytic metal or alloy, such as platinum-iridium wire heated to 600-800 degrees Celsius. One bead is coated with a reactive catalyst. In the presence of a flammable gas, the heat of oxidation raises the temperature of the bead and alters the electrical resistance characteristics of the measuring circuit. This resistance change is related to the concentration of all flammable gases, including hydrogen, in the vicinity of the sensor.

Sensors of such "hot wire" type have cross-sensitivity to other easily oxidized materials, such as alcohols and hydrocarbons. Such easily oxidized materials are common components of gases in a semiconductor-manufacturing environment, and often result in the frequent occurrence of false alarms.

Current hot wire sensors require an oxidation reaction for operation, such sensors are unable to detect hydrogen when it is present in inert gas streams or environments which are not of a character to support an oxidative reaction. This is a deficiency of such hot wire sensors and limits their applicability and utility.

The CC sensor has drawbacks. In oxygen deficient environments or above an upper explosive limit, the oxidation process is quenched causing difficulties in measuring. In addition, since the CC sensor is based upon oxidation, and all hydrocarbons have the same response as hydrogen, this makes it difficult to detect hydrogen in environments which also contain hydrocarbons. Further, the CC sensor element is easily contaminated by halogenated hydrocarbons and is susceptible to poisoning by silicones, lead and phosphorous.

Another commonly used hydrogen sensor is a non-porous metal oxide (MO) sensor. The MO sensor element comprises a non-porous metal oxide (such as zirconium dioxide or tin dioxide) sandwiched between two porous metal electrodes. Such electrodes are typically made of platinum. One electrode is exposed to the reference gas, usually air, and the other electrode is exposed to the test gas being detected.

Mobile ions diffuse to both surfaces of the oxide where they may be eliminated by reaction with adsorbed species. In the absence of gas species which can be oxidized (such as, for instance, carbon monoxide or hydrogen), the electrochemical potential of the sensor may be determined by the Nernst equation and is proportional to the partial pressure of oxygen in the test gas only. In order to achieve sensitivity to hydrogen with this device, the platinum electrode is co-deposited with gold. Since gold is a substantially less efficient donor of electrons than platinum, oxidation rates are reduced, equilibrium conditions are not achieved and the sensor becomes sensitive to the composition of the test gas. The electrochemical potential which develops becomes "non-Nernstian", and is a complicated function of the kinetics and mass transfer associated with all species reacting at the electrode.

Like the CC sensor, the MO sensor has serious disadvantages. The sensor is not hydrogen-specific and all oxidizable gases in the test gas contribute to the sensor signal. The response is relatively slow and it can take up to 20 seconds to reach 50% of maximum signal when exposed to 1% hydrogen in air at flows below 200 standard cubic centimeters per minute (sccm); the recovery time is even slower taking up to 5 minutes to reach 50% of maximum signal when exposed to less than 200 sccm of air. Finally, in order to achieve even these orders of response time, the device must be operated at temperatures above 350 degrees Celsius. Operating at such temperatures, is potentially unsafe and may cause ignition and/or explosion.

Another class of sensors includes metal-insulator semiconductor (MIS) or metal-oxide-semiconductor (MOS) capacitors and field effect transistors, as well as palladium-gated diodes. In general however, these sensors are limited to detecting low concentrations of hydrogen.

Yet another type of sensor is the metal oxide-semiconductor (MOS) sensor which is also known and is mentioned, for instance, in the U.S. Pat. No. 6,006,582 to Bhandari, et. al. The MOS sensor element comprises an oxide, typically of iron, zinc, or tin, or a mixture thereof, and is heated to a temperature of about 150 degrees Celsius to about 350 degrees Celsius. Bhandari et. al. reported that oxygen absorbs on the surface of the sensor element to create an equilibrium concentration of oxide ions in the surface layers.

The original resistance of the MOS sensor is first measured. When certain compounds, such as, for instance, CO, or hydrocarbons come in contact with the sensor, they are adsorbed on the surface of the MOS element. This absorption shifts the oxygen equilibrium, causing a detectable increase in conductivity of the MOS material.

MOS hydrogen sensors have a number of operational deficiencies and are, therefore, unsatisfactory in many respects. They require frequent calibration and their response times are too long (up to 3-5 minutes). Bhandari et. al. noted that the MOS sensors are unsafe and can cause ignition and explosion, and are susceptible to being poisoned with halogenated vapors. Like the CC and the MO sensors discussed above, they are not hydrogen specific. All volatile organic compounds as well as gases containing hydrogen will react with the sensor materials in the sensing elements of these detectors, thereby providing false readings.

Still yet another sensor is the catalytic gate (CG) sensor, the simplest embodiment of which is a MOS structure, where the metal is usually platinum or palladium deposited on an insulator, such as silicon dioxide. Hydrogen dissociates on platinum or palladium and subsequently diffuses into the bulk of the metal. Hydrogen atoms which arrive at the metal-insulator interface, form a dipole layer, polarizing the interface and consequently changing its electrical characteristics. The CG sensor also has serious drawbacks, particularly slow response time when the surface is contaminated. The surface of platinum or palladium is very much susceptible to contamination and poisoning.

There exists no known prior art teaching of a hydrogen-specific sensor, which quickly responds only to hydrogen gas at room temperature and which is not susceptible to poisoning. Yet, as discussed above, such sensor is highly desirable and the need for such sensor, which is also low cost, lightweight and of a miniature size, is acute.

The present invention discloses such a sensor. It therefore is an object of the present invention to provide an improved hydrogen selective sensor and hydrogen sensing methodology overcoming the aforementioned deficiencies of the previously known hydrogen detectors.

Because hydrogen is used in such a wide variety of environments, it is desirable to have a sensor that will be reproducible and specific to hydrogen, even with varying concentration of background gases such as oxygen, water and other contaminants.

It is also desirable to have a solid state sensor, operating at room temperature, that has no moving parts, has a response time on the order of seconds, would operate with minimum power consumption, does not require frequent calibration, and could be used in a hand-held portable instrument.

SUMMARY OF THE INVENTION

It therefore is one object of the present invention to provide an improved hydrogen sensor.

It is another object of the invention to provide a hydrogen sensor that detects only the presence of hydrogen at room temperature.

It is another object of the invention to provide a hydrogen sensor that senses the presence of hydrogen, at room temperature, in a reproducible and hydrogen-specific manner.

It is another object of the invention to provide a hydrogen sensor that senses the presence of hydrogen, at room temperature, in a reproducible and hydrogen-specific manner, even with varying concentrations of background gases such as oxygen, water and other contaminants.

It is another object of the invention to provide a hydrogen sensor that senses the presence of hydrogen, at room temperature, in a reproducible and hydrogen-specific manner, even with varying concentrations of background gases such as oxygen, water and other contaminants and is self-cleaning in nature.

One aspect of the present invention embodiments relates to a method of detecting hydrogen in an environment comprising:

providing a MEMS based hydrogen sensor device comprising a substrate, a hydrogen-sensitive thin film with the hydrogen-sensitive thin film being comprised of a sol-gel coating of nanostructured indium oxide doped tin oxide, with nanostructured $BaCeO_3$ and Pt and other metal-catalyst overlayers, arranged for exposure to the environment and exhibiting a detectable change of physical property when the hydrogen-sensitive thin film is exposed to hydrogen at room temperature;

exposing the hydrogen-sensitive thin film based MEMS device to the environment;

outputting said detectable change of physical property when the presence of hydrogen in the environment is detected; and exposing the MEMS based hydrogen sensor device to an ultra-violet light source as a mean for regenerating and decontaminating the MEMS device (self-cleaning).

It is yet another object of the present invention to provide a solid state micro electro-mechanical systems (MEMS) hydrogen-selective sensor that has no moving parts, has a response time on the order of seconds, operates with minimum power consumption, does not require frequent calibration, has a large dynamic detection range, can operate at room temperature, and can be readily embodied as a hand-held portable instrument.

The present invention relates in one aspect to a hydrogen sensor platform, comprising a hydrogen-sensitive thin film sensor element on a silicon (Si) wafer substrate wherein the hydrogen sensor platform receives a sol-gel coating of an indium oxide doped tin oxide thin film over the sensor platform.

In another embodiment the MEMS substrate having a sol-gel coating of an indium oxide doped tin oxide thin film is exposed to an ultra violet light source as a means for removing contaminants and regenerating (self-cleaning) the MEMS hydrogen-selective sensor device.

In embodiments the insulating oxide layer may be thermally grown on the substrate surface or deposited by other methods such as vapor deposition or sputtering.

Another aspect of the present invention relates to the patterning of electrodes onto the MEMS device using known techniques, for example, photolithography or wet chemical etching. In embodiments, the patterning of each electrode is carried out using positive or negative photoresist, or a known lift-off method.

In one embodiment, the hydrogen-sensitive, indium oxide doped tin oxide thin film is overlaid by a hydrogen-selective layer protecting the thin film hydrogen-sensor from deleterious interaction with non-hydrogen components of the environment being monitored, such as carbon monoxide, carbon dioxide, alcohols, hydrogen sulfide, ammonia, and hydrocarbons etc. The hydrogen-selective layer may include nanostructured barium cerate, or strontium cerate or other proton conducting membranes and the nanoclusters of catalyst may include a metal such as Pt, Pd, Au, Ag or Rh, and/or alloys thereof.

In another embodiment, the sol-gel derived nanostructured indium oxide ($In_2O_3$) doped tin oxide ($SnO_2$), with the sol-gel or microemulsion derived hydrogen-selective overlayer, is dip-coated over the hydrogen sensor platform before being wire-bonded to a plastic or ceramic package.

Other objects and advantages of the present invention will be more fully apparent from the ensuing disclosure, illustrations, and appended claims.

BRIEF DESCRIPTION OF THE FIGURES

FIG. 2A illustrates the silicon substrate used for fabricating the hydrogen sensor.

FIG. 2B illustrates the oxidation step used for fabricating the hydrogen sensor.

FIG. 2C illustrates the metallization step used for fabricating the hydrogen sensor.

FIG. 2D illustrates photolithography/etching step used for fabricating the hydrogen sensor.

FIG. 2E illustrates the application and coating of Nanomaterials onto the substrate of the hydrogen sensor.

FIG. 2F illustrates the wire bonding fabrication step.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

The present invention relates to a micro electro-mechanical systems (MEMS) hydrogen sensor which integrates a nanostructured indium oxide doped tin oxide thin film hydrogen sensor element, made using a sol-gel dip-coating process, with an ultra-violet light source as a means for decontaminating and regenerating the MEMS based hydrogen sensor. The hydrogen sensor of the invention is a MEMS device that may be adapted in a variety of apparatus embodiments to accommodate the objects of the invention.

The MEMS device of the present invention may be fabricated in a number of ways, for example, the MEMS device may be formed from a substrate. Typical substrates may comprise a silicon wafer or glass with an oxide layer added for insulation.

In embodiments, the substrate of the present invention may, for example, comprise a silicon wafer having a thickness of from about 5 micrometers (µm) to about 5 inches as shown schematically in FIG. 2A.

In other embodiments, the thickness of the substrate may range from about 1 to about 5 inches. In a specific embodiment, the thickness of the substrate is from about 3 inches.

The substrate is oxidized to provide an insulating layer of silicon dioxide, as illustrated schematically in FIG. 2B. In various embodiments of the instant invention, the oxidizing layer varies in thickness from about 0.05 to about 2 micrometers (µm). In a specific embodiment, oxide layer is about 0.5 micrometers (µm).

The substrate may be oxidized thermally in air at a temperature of from about 100 to about 600 degrees Celsius for from about 1 to about 3 hours. In a specific embodiment, the substrate is oxidized thermally in air at from about 100 to about 200 degrees Celsius for 1 hour.

After photolighography or electron beam lithography, the electrode is patterned using known methods such as, for example, wet or dry etching as illustrated in FIG. 2D. Alternatively, a lift-off technique can be used, in which patterning is achieved by the dissolution of photoresist followed by deposition of a metallic layer of photolithographically or e-beam lithographically defined photoresist layer.

The physical gap between the electrodes varies in embodiments from about 100 nanometers (nm) to about 100 micrometers (µm). In a specific embodiment, the gap varies from about 10 to about 50 µm.

Figure 1B:
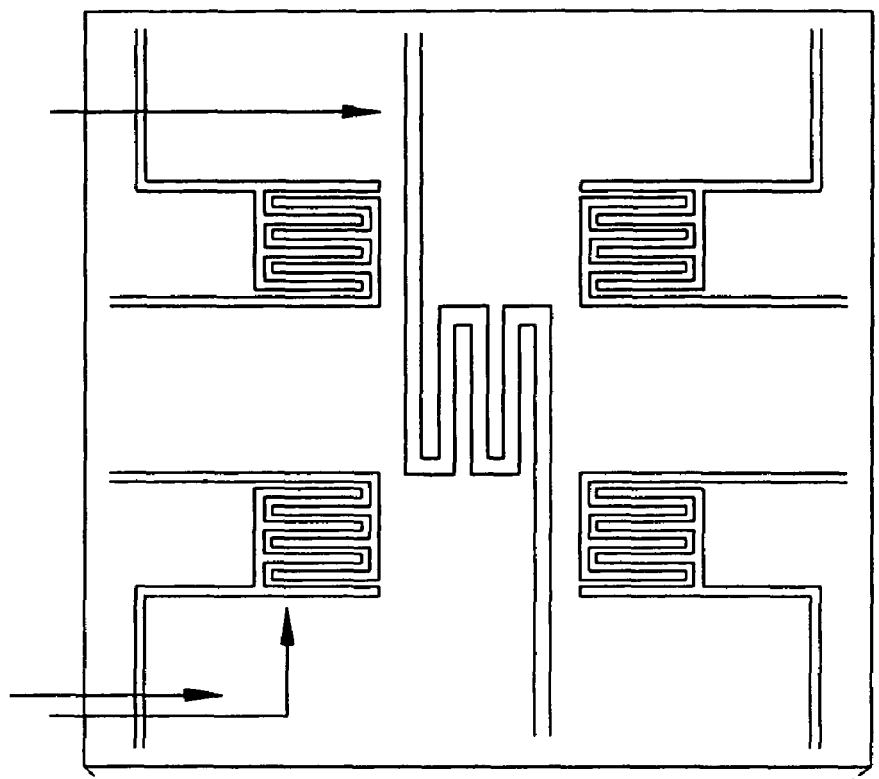
FIG. 1B is an exploded view of the same mask design showing the resistive temperature sensor of the hydrogen micro sensor.
Figure 1A:
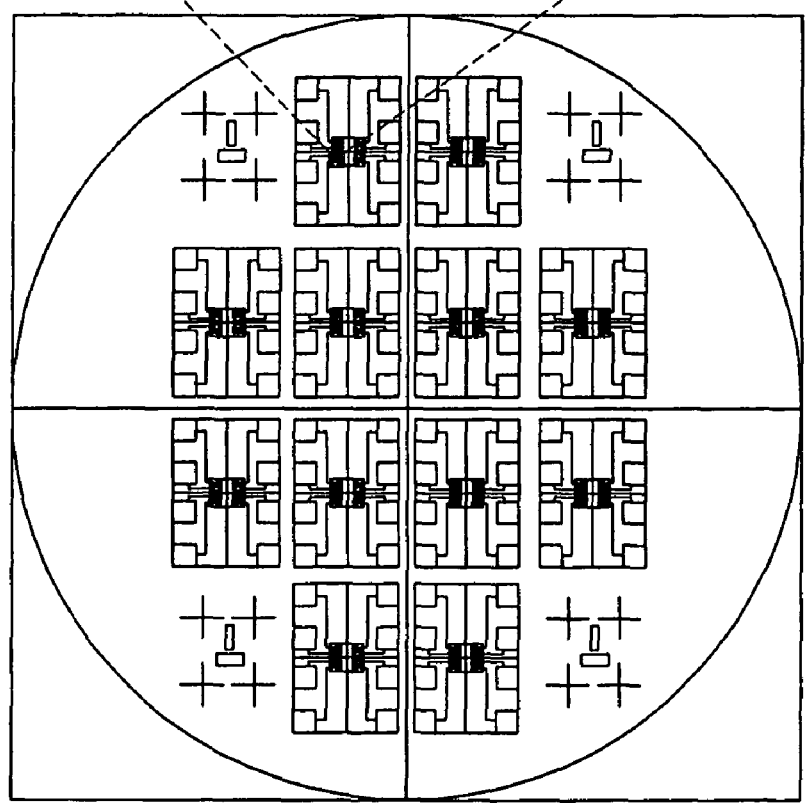
FIG. 1A is a top view of one embodiment showing the mask design of the hydrogen micro sensor.
Figure 3:
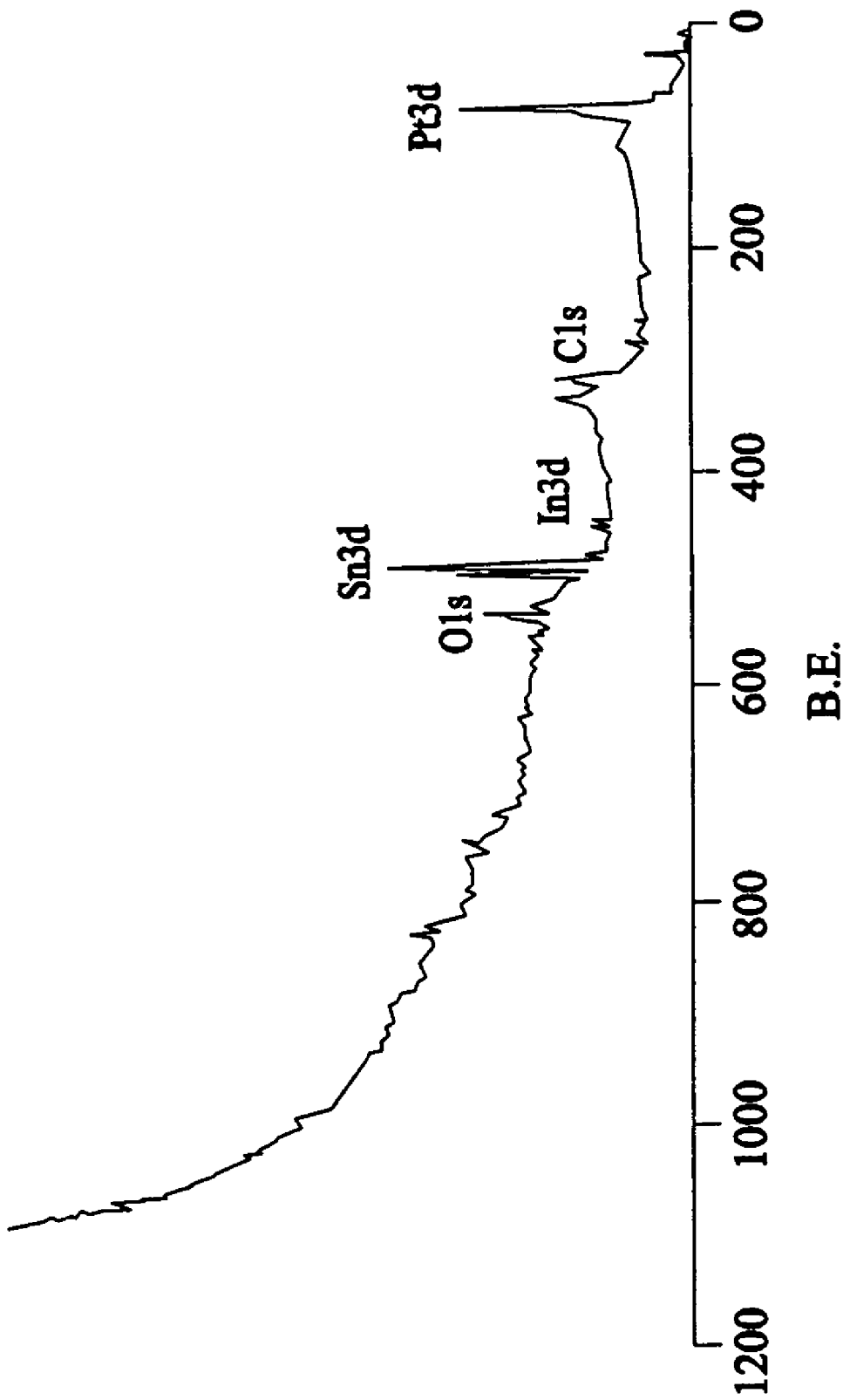
FIG. 3 illustrates XPS analysis of sol-gel sip-coated MEMS device showing the presence of In, Sn, O, and Pt.

In embodiments, a sol-gel process is used for coating the indium oxide ($In_2O_3$) doped tin oxide ($SnO_2$) as shown in FIG. 2E. The chemistry of the nanoparticles are listed in FIG. 3 (XPS spectrum). In addition to tin oxide, other oxides, such as, for example, titania ($TiO_2$), iron oxide ($Fe_2O_3$), and zinc oxide (ZnO) are suitable for embodiments of the present invention.

The sol-gel process is a versatile solution process for making ceramic and glass materials. In general, the sol-gel process involves the transition of a system from a liquid "sol" (mostly colloidal) into a solid "gel" phase. Applying the sol-gel process, it is possible to fabricate ceramic or glass materials in a wide variety of forms: ultra-fine or spherical shaped powders, thin film coatings, ceramic fibers, microporous inorganic membranes, monolithic ceramics and glasses, or extremely porous aerogel materials. The starting materials used in the preparation of the "sol" are usually inorganic metal salts or metal organic compounds such as metal alkoxides. In a typical sol-gel process, the precursor is subjected to a series of hydrolysis and polymerization reactions to form a colloidal suspension, or a "sol". Further processing of the "sol" enables one to make ceramic materials in different forms. Thin films can be produced on a piece of substrate by spin-coating or dip-coating. When the "sol" is cast into a mold, a wet "gel" will form. With further drying and heat-treatment, the "gel" is converted into dense ceramic or glass articles. If the liquid in a wet "gel" is removed under a supercritical condition, a highly porous and extremely low density material called "aerogel" is obtained. As the viscosity of a "sol" is adjusted into a proper viscosity range, ceramic fibers can be drawn from the "sol". Ultra-fine and uniform ceramic powders are formed by precipitation, spray pyrolysis, or emulsion techniques.

In embodiments of the present invention a sol-gel coating comprising an indium oxide doped tin oxide thin film is applied over the hydrogen sensor MEMS platform using known coating techniques such as, for example, spin or dip coating. After the application of the nanomaterial ($In_2O_3$ doped $snO_2$), the material is then dried at a temperature of from about 100 to about 200 degrees Celsius. Annealing is carried out at temperature of about 300 to about 1000 degrees Celsius after sputtering a thin film of Pt over the sensor-material.

Once the hydrogen-sensing layer has been formed, a hydrogenselective layer is deposited over the hydrogen-sensing layer. This hydrogen-selective overlayer may be comprised of a barium cerate or strontium cerate or other proton conducting membrane with the surface metal catalyst which may be of platinum, palladium, gold, silver, rhuthenium, and/or alloys thereof. In embodiments, the hydrogen-sensitive layer has a thickness of from about 100 to about 500 nanometers. In one specific embodiment, the hydrogen-sensitive thin film having thickness of 100 to 150 nanometer (nm) is deposited followed by a hydrogen-selective layer of barium cerate overlayer and Pt catalyst having a thickness of from about 5 to about 50 nanometers, as illustrated schematically in FIG. 2E.

As a further variation, the hydrogen-selective over layer may be formed of nanostructured barium cerate, strontium cerate or other proton conducting membrane or hydrogen permable membranes. For example, the thickness of the hydrogen-sensitive material thin films ranges from about 100 to about 500 nm thick, more specifically from about 100 to about 150 nm thick, with a hydrogen-selective layer when present having a thickness of from about 5 to about 50 nm, and more specifically from about 5 to about 20 nm. The hydrogen-selective over layer is, in embodiments, thick enough to adequately protect the sensor from other gases in the environment and thin enough to leave unchanged the properties being monitored in the operation of the device.

The hydrogen-selective over-layer may be deposited or formed over the hydrogen-sensitive film in any suitable manner, including spraying, solution deposition (sol-gel and microemulsion and other techniques), dipping , chemical vapor deposition, physical vapor deposition, focused ion beam deposition, sputtering, etc. Generally, the methods described herein for formation or coating of the hydrogen-sensitive thin film in the first instance may also be used for forming the hydrogen-selective over-layer thereon, and vice versa.

The hydrogen-selective over-layer may be formed of any suitable material of construction, which is suitably effective to prevent chemical reaction or sorption processes from occurring that would preclude the efficacy of the hydrogen-sensing film for hydrogen sensing.

The selectivity exhibited by the proton conducting membrane films allows, for the first time, fabrication of inexpensive hydrogen sensors that can be deployed in large numbers to remotely monitor hydrogen levels over large areas. Furthermore, hydrogen-selective films can operate in an industrial or manufacturing environment containing trace organic vapors.

The hydrogen sensing films can be coated with materials such as nanostructured barium cerate, stronsium cerate or other proton conducting membranes or hydrogen permeable membranes to provide an effective barrier to the other gases in the environment, yet enable only hydrogen to diffuse through to the hydrogen-sensing thin film, thereby acting as a selective membrane for hydrogen in the sensor element.

The hydrogen-sensing thin film sensor element of such a hydrogen sensor may comprise a semiconductor thin film (i) arranged for exposure to an environment susceptible to the incursion or generation of hydrogen and (ii) exhibiting a detectable change of physical property when the hydrogen sensing film is exposed to hydrogen. Such detectable change of physical property may comprise optical transmissivity, electrical resistivity, electrical conductivity, electrical capacitance, magneto-resistance, photoconductivity, and/or any other detectable property change accompanying the exposure of the thin film sensor element to hydrogen. The hydrogen sensor may further include a detector constructed and arranged to convert the detectable change of physical property to a perceivable output, e.g., a visual output, auditory output, tactile output, and/or auditory output.

Figure 4:
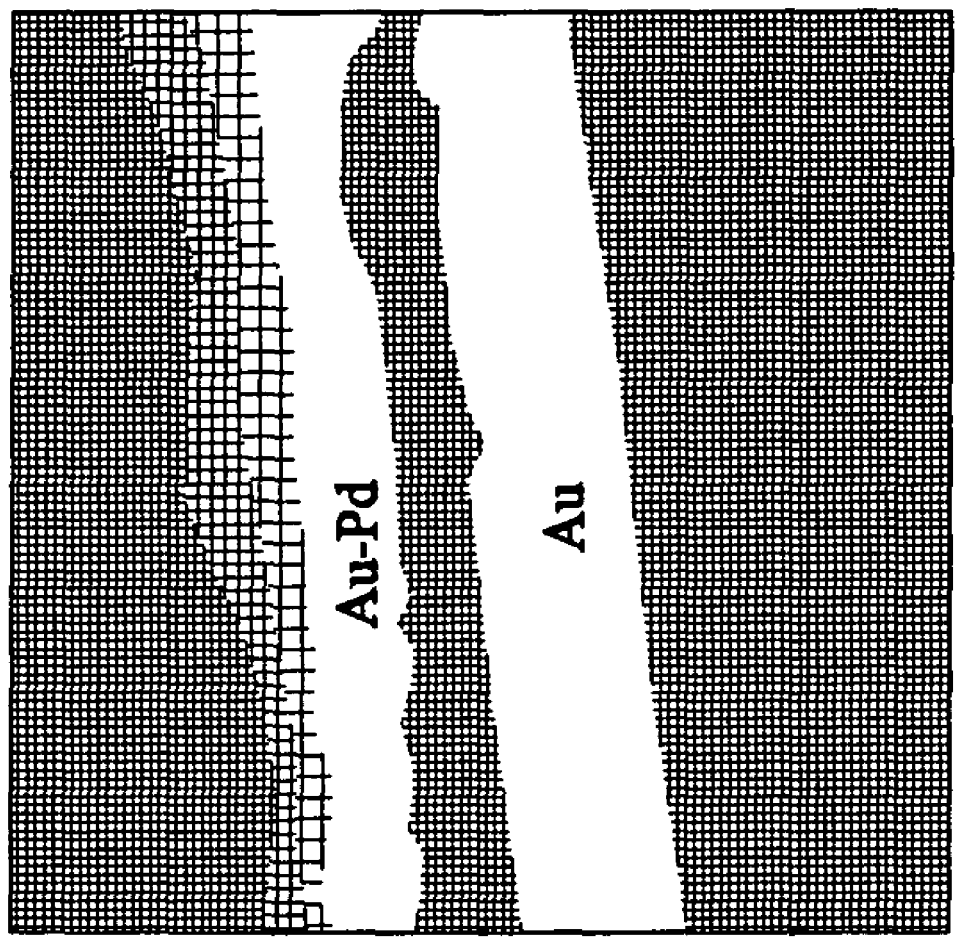
FIG. 4 illustrates multilayer structure of MEMS-based hydrogen sensor, which is an enlarged view of an encircled portion in FIG. 2E.

The MEMS hydrogen sensor platform is then bonded using known techniques such as, for example, wire-bonding, ball-bonding, or flip-chip bonding as shown schematically in FIG. 2F and the cross section is shown in FIG. 4.

Wire bonding is an electrical interconnection technique using thin wire and a combination of heat, pressure and/or ultrasonic energy. Wire bonding is a solid phase welding process, where the two metallic materials (wire and pad surface) are brought into intimate contact. Once the surfaces are in intimate contact, electron sharing or interdiffusion of atoms takes place, resulting in the formation of wire bond. In wire bonding process, bonding force can lead to material deformation, breaking up contamination layer and smoothing out surface asperity, which can be enhanced by the application of ultrasonic energy. Heat can accelerate interatomic diffusion, thus the bond formation.

The Wire bonding process begins by firmly attaching the backside of a chip to a chip carrier using either an organic conductive adhesive or a solder (Die Attach). The wires then are welded using a special bonding tool (capillary or wedge). Depending on bonding agent (heat and ultrasonic energy), the bonding process can be defined to three major processes: the microcompression bonding (T/C), ultrasonic bonding (U/S), and thermosonic bonding (T/S), as shown in Table A1.

TABLE A1

Three wire bonding processes.

| Wire bonding | Pressure | Temperature | Ultrasonic energy | Wire | Pad |
| --- | --- | --- | --- | --- | --- |
| Thermo compression | High | 300-500° C. | No | Au, | Al, Au |
| Ultrasonic | Low | 25° C. | Yes | Au, Al | Al, Au |
| Thermo sonic | Low | 100-150° C. | Yes | Au | Al, Au |

The method of wire bonding that is most popular today is gold ball bonding, a process that melts a sphere of gold on a length of wire, bonds that down as a first bond, draws a loop out, and then connects the wire bond (the second wedge bond) down by means of a crescent and then reforms another ball for the subsequent first ball bond.

Flip chip microelectronic assembly is the direct electrical connection of face-down (hence, "flipped") electronic components onto substrates, circuit boards, or carriers, by means of conductive bumps on the chip bond pads. In contrast, wire bonding, the older technology which flip chip is replacing, uses face-up chips with a wire connection to each pad.

Flip chip components are predominantly semiconductor devices; however, components such as passive filters, detector arrays, and MEMS devices are also beginning to be used in flip chip form. Flip chip is also called Direct Chip Attach (DCA), a more descriptive term, since the chip is directly attached to the substrate, board, or carrier by the conductive bumps.

Eliminating packages and bond wires reduces the required board area by up to approximately 95%, and requires far less height. Weight can be less than approximately 5% of packaged device weight. Flip chip is the simplest minimal package, smaller than Chip Scale Packages (CSP's) because it is chip size.

Figure 5:
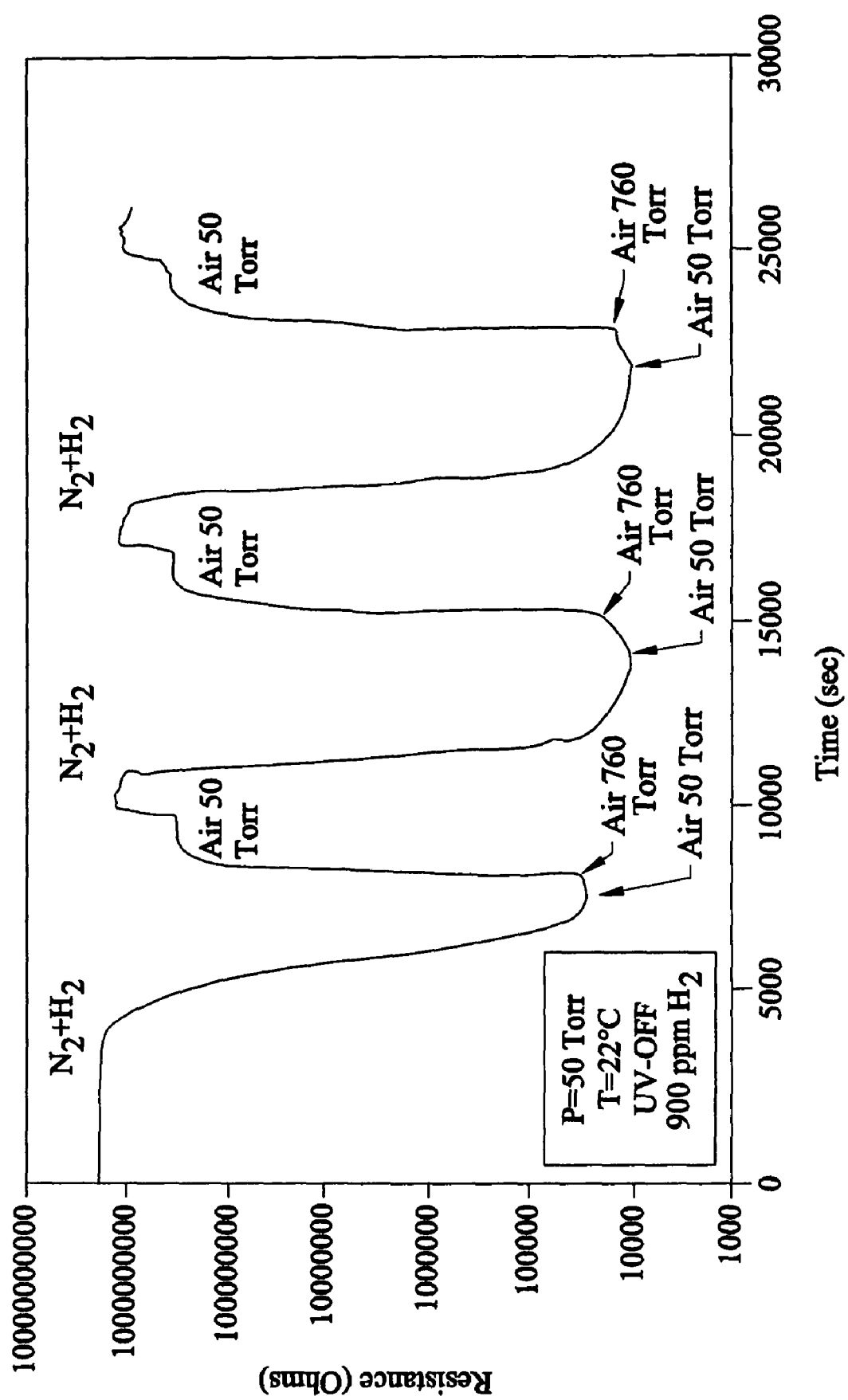
FIG. 5 illustrates giant-room temperature hydrogen sensitivity for the MEMS based sensor.

There are three stages in making flip chip assemblies: bumping the die or wafer, attaching the bumped die to the board or substrate, and, in most cases, filling the remaining space under the die with an electrically non-conductive material. The conductive bump, the attachment materials, and the processes used differentiate the various kinds of flip chip assemblies In embodiments, a ultra-violet light source is assembled facing the MEMS based hydrogen sensor. The UV light source is used for burning organic contaminates from the MEMS device and as a light source. This decontamination produces a clean sensor surface suitable for sensing hydrogen at room temperature. The UV source is turned off during hydrogen sensing tests and the sensor detects hydrogen very efficiently at room temperature. (FIG. 5 shows a giant room temperature sensitivity).

The MEMS based hydrogen sensor device may be connected by a signal transmission line to the central processor unit, which may comprise microprocessor or computer control elements for actuation, monitoring and control of the hydrogen sensor device. The central processor unit processes the signal carried by signal transmission line, and produces an output signal that is transmitted in signal transmission line to an output device, which produces an output that is indicative of the presence or absence of hydrogen in the environment to which the sensor is exposed.

The output of the central processor unit may include any perceivable output, such as auditory output, visual output, tactile output (as for example when the hydrogen sensor apparatus is adapted to be worn on the body of a user, and the central processor unit comprises a vibrator imparting vibratory sensation to the user's body when hydrogen is detected in the environment, such as may be useful in environments where auditory or visual outputs are not readily perceivable.

In lieu of producing an output which is perceivable, the central processor unit 44 may be programmed to actuate means for eliminating hydrogen from the environment being monitored, as for example a sweep gas flushing operation to purge the environment of the hydrogen gas.

In embodiments, the MEMS base hydrogen senor operates in wide temperature of from about 15 degrees Celsius to about 650 degrees Celsius.

EXAMPLE 1

MEMS Based Sensor Platform Fabrication

A 3" Si (100) wafer is used as a substrate for sensor fabrication. On top of the substrate 0.1 to 1 mm of silicon oxide is thermally grown. Alternatively, oxide can be deposited by other methods such as CVD or sputtering. Oxide is used as an insulation layer. Alternatively, glass substrate can be used. 10-50 nm-thick chromium (Cr) or titanium (Ti) and 100-500 nm-thick gold (Au) films are deposited by thermal or e-beam evaporation on top of the oxide layer or on the glass substrate. The interdigitated electrodes were patterned on the substrate using photolithography and wet chemical etching. Positive or negative photoresist was used for patterning the electrodes. Alternatively, a lift-off method is used to pattern the electrodes. The gap between electrodes is kept in the range of 10 nm to 50 mm. After sol-gel coating of $In_2O_3$ doped-$SnO_2$ thin films over the sensor platform, in which coating process is outlined in the following section, the MEMS sensor platform is wire-bonded to a plastic or ceramic package as illustrated in FIG. 2 schematically.

EXAMPLE 2

Tin(IV)-isopropoxide ($Sn[OC_3H_7]_4$) (10 w/v %) in iso-propanol (72 vol. %) and toluene (18 vol. %) and indium(III)-isopropoxide ($In[OC_3H_7]_3$) are prepared and mixed. Small glass substrates (1cm×1cm) are cut from the Pyrex glass slides for the dip-coating experiments. The tin oxide ($SnO_2$) semiconductor thin film coating, in doped and undoped forms, is combined on the Pyrex glass (silica) slides (substrate) and fabricated via sol-gel dip-coating technique. The glass substrates are ultrasonically cleaned, first in acetone and then in iso-propanol. The pre-cleaned substrates are dipped in the solution of tin-isopropoxide in iso-propanol and toluene, having a concentration of 0.23 M of tin-isopropoxide, using a dip-coater with a withdrawal speed of 150 cm/min. Indium (III)-isopropoxide is dissolved in this solution to obtain thin films of $SnO_2$ containing 6.5 mol % $In_2O_3$. The gel films formed are dried at a temperature of from about 150 to about 200 degrees Celsius for about 1 hour in air. The substrates are then dip-coated again using the same solution under similar conditions and dried again at from about 150 to about 200 degrees Celsius for about 1 hour in air. A thin layer of Platinum is sputtered for about 10 sec on the dried thin films using a sputter coater. The dried and Pt-sputtered gel films are then fired at a temperature of from about 400 to about 600 degrees Celsius in air. The samples are heated at a rate of about 30° C./min up to the firing temperature, held at that temperature for about 1 h, and then cooled to room temperature (20° C.) inside the furnace.

EXAMPLE 3

Fabrication of a MEMS Based Hydrogen Sensor

Micro structures were fabricated through a commercial foundry and the as-received die was micro machined using $XeF_2$ as a silicon selective etchant. A photolithographic lift-off process was used in combination with physical vapor deposition (PVD) to sequentially deposit a gold/titanium thin film overlaid by a indium oxide doped tin oxide on the suspended micro structures. The resulting devices were wire bonded and packaged in 40 pin ceramic chip carriers.

The fully packaged chips were placed in a sealed chamber, and electrical contact made via feedthroughs into the chamber. Nitrogen and hydrogen were introduced into the chamber and controlled with mass flow controllers and actuated valves. The resistance of the sensing film was measured periodically with a digital multimeter and logged on a desktop computer.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A hydrogen sensor device that detects hydrogen at room temperature, comprising:
   (a) a micro electro-mechanical system (MEMS) formed on a substrate comprising:
      (i) a semiconductor substrate;
      (ii) an oxidized layer over said substrate;

(iii) an interdigitated electrode configuration formed over said oxidized layer;

(b) a hydrogen sensitive semiconductor oxide thin film over the interdigitated electrodes;

(c) a hydrogen-selective membrane layer formed over the hydrogen-sensitive semiconductor oxide thin film; and (d) a detector for detecting presence of hydrogen from the hydrogen senser device by measuring a change of an electrical property at room temperature; and (e) an ultra-violet source focused on said hydrogen-selective membrane layer for regenerating and decontaminating the hydrogen sensor device.

2. The hydrogen sensor device according to claim 1 wherein said semiconductor substrate is comprised of silicon (Si).

3. The hydrogen sensor device according to claim 1 wherein said semiconductor substrate is comprised of glass.

4. The hydrogen sensor device of claim 1, wherein said hydrogen sensitive semiconductor oxide thin film comprises nanostructured indium oxide doped tin oxide.

5. The hydrogen sensor device of claim 1, wherein said hydrogen-selective membrane layer is selected from platinum, palladium, gold, silver, or rhuthenium.

6. The hydrogen sensor device of claim 1, wherein said hydrogen sensitive semiconductor oxide thin film has a thickness of from about 100 nm to about 500 nm.

7. The hydrogen sensor device of claim 1, wherein said hydrogen-selective membrane layer has a thickness of from about 5 nm to about 50 nm.

8. The hydrogen sensor device of claim 1, wherein said hydrogen sensitive semiconductor oxide thin film is formed by a sol-gel process is comprised of a dopant in tin oxide.

9. The hydrogen sensor device of claim 8, wherein said dopant is comprised of about 5 to about 15 mole percent of indium-oxide.

10. The hydrogen sensor device of claim 9, wherein said dopant is comprised of about 6.5 mole percent of indium-oxide.

11. The hydrogen sensor device of claim 1, wherein said interdigitated electrode configuration has an electrode gap of about 20 micrometers.

12. The hydrogen sensor device of claim 9, wherein said indium oxide doped tin-oxide hydrogen sensitive semiconductor oxide thin film is deposited on the interdigitated electrode configuration.

13. The hydrogen sensor device of claim 1, wherein the detector includes detecting a detectable change of a physical property comprised of electrical resistivity or electrical conductivity of the hydrogen sensitive semiconductor oxide thin film.

14. The hydrogen sensor device of claim 13, wherein the detector includes an output selected from the group consisting of visual outputs, auditory outputs, tactile outputs, and auditory outputs.

15. The hydrogen sensor device of claim 1, wherein said detectable change of the electrical property occurs when the hydrogen sensitive semiconductor oxide thin film sensor is contacted with hydrogen gas.

16. The hydrogen sensor device of claim 1, further comprising a power supply for the hydrogen sensor device.

17. The hydrogen sensor device of claim 1, where in said device detects the hydrogen at room temperature and air-pressure within the range of about 50 to about 760 Torr, and with hydrogen selectivity over carbon monoxide, carbon dioxide, nitrogen monoxide, nitrogen dioxide, and hydrogen sulfide with a detection and recovery time of about 50 to about 200 sec.

18. The hydrogen sensor device of claim 17, wherein the hydrogen is detected up to about 900 ppm.

* * * * *

UNITED STATES PATENT AND TRADEMARK OFFICE
CERTIFICATE OF CORRECTION

| | | |
|---|---|---|
| PATENT NO. | : 7,791,150 B1 | Page 1 of 1 |
| APPLICATION NO. | : 10/949600 | |
| DATED | : September 7, 2010 | |
| INVENTOR(S) | : Sudipta Seal et al. | |

It is certified that error appears in the above-identified patent and that said Letters Patent is hereby corrected as shown below:

Column 1, line 3 insert:

-- STATEMENT REGARDING FEDERALLY SPONSORED RESEARCH OR DEVELOPMENT:

The subject invention was made with government support under the National Science Foundation (NSF) Grant EECS 0801774 and the National Aeronautics and Space Administration (NASA) Grant NAG 32751. The government has certain rights to this invention. --

Signed and Sealed this
Nineteenth Day of April, 2011

David J. Kappos
*Director of the United States Patent and Trademark Office*